United States Patent [19]

Calvo

[11] Patent Number: 4,556,554

[45] Date of Patent: Dec. 3, 1985

[54] IMMOBILIZED ENZYMES

[75] Inventor: Luis C. Calvo, Bayshore, N.Y.

[73] Assignee: Germaine Monteil Cosmetiques Corp., Deer Park, N.Y.

[21] Appl. No.: 269,935

[22] Filed: Jun. 1, 1981

[51] Int. Cl.[4] .......................... A61K 7/06; A61K 31/74
[52] U.S. Cl. ................... 424/70; 424/DIG. 1; 424/DIG. 2; 424/DIG. 4; 424/78; 514/844; 514/845; 514/847; 514/848; 514/852; 514/859; 514/861; 514/864; 514/880; 514/881
[58] Field of Search ...................... 424/70, 78, 81, 358, 424/80, 94

[56] References Cited

U.S. PATENT DOCUMENTS

| 2,056,358 | 10/1936 | Malone | 424/94 X |
| 2,977,287 | 3/1961 | Block et al. | 424/94 X |
| 2,995,493 | 8/1961 | Douglas et al. | 424/94 X |
| 3,070,497 | 12/1962 | Knight | 424/94 |
| 3,173,847 | 3/1965 | Kita et al. | 424/94 X |
| 3,576,760 | 4/1971 | Gould et al. | 424/94 X |
| 3,964,973 | 6/1976 | Hradil et al. | 424/94 X |
| 3,981,996 | 9/1976 | Leigh | 424/94 |
| 4,122,158 | 10/1978 | Schmitt | 424/94 |
| 4,144,131 | 3/1979 | Richardson | 424/94 X |
| 4,261,969 | 4/1981 | Heller | 424/94 X |
| 4,273,873 | 6/1981 | Sugitachi et al. | 424/94 |

OTHER PUBLICATIONS

Kindel Enzymes, "The Bioindustrial Revolution", Technology, 11/12/1981, pp. 62 to 74.

*Primary Examiner*—Dale R. Ore
*Attorney, Agent, or Firm*—Wolder, Gross & Yavner

[57] ABSTRACT

A cosmetic composition is provided for the removal of sebum exudate from the skin. The composition comprises immobilzed enzymes in cosmetically acceptable vehicles for topical application. The immobilized enzymes are lipolytic lipases, proteolytic proteases and enzymes for the breakdown of sugar oligomers from glucoproteins in the skin exudates. The enzymes may be present individually or in any desired combination. The enzymes are immobilized in known manners by chemical and or physical means and are released from immobilization upon application to the skin.

10 Claims, No Drawings

IMMOBILIZED ENZYMES

FIELD OF THE INVENTION

This invention relates to cleansing cosmetics and more particularly to cosmetics containing immobilized enzymes in cosmetically acceptable vehicles to provide for the release of enzyme activity for cosmetic and cleansing purposes.

BACKGROUND OF THE INVENTION

The skin is an important secretory and excretory organ of the body. Water is transpired through the skin. It also serves to excrete certain glycoid and nitrogenous wastes via apocrine perspiration. In addition hair grows from the skin and sebum is secreted.

Sebum is a holocrine secretion of the sebaceous glands. It is a thick semifluid secretion composed of fatty material and epithelial debris from the cells of the malpighian layer. The sebaceous glands are scattered over the surface of the skin. They lie in the derma layer of the skin and generally their excretory duct opens into the neck of a hair sac.

The largest sebaceous glands are on and around the nose, forehead and the ears. Thus the largest quantity of sebum is secreted in the most visible areas of the person. Given present fashion, this oily residue on the skin surface presents a cosmetic problem.

Sebum itself results from the normal destruction of the epithelial cells followed by regeneration of the numerous epithelial elements. In the body of the sebaceous gland, mitosis is numerous in the cells close to the walls of the excretory ducts along the hair shaft wherein the new cells form replacements and move into the secretory regions. Thus the base of the hair, where the sebum emerges from the skin, is coated with oils and a proteinaceous mixture composed of exfoliated cellular debris. This, too, presents a cosmetic problem which is solved by shampooing regularly. Much of dandruff, decried in the advertisements as a social disease, is this exfoliation of the epithelial cells.

While anatomically sebum is the combined excretion of the dead cellular matter, the fatty oils and water, the term most commonly refers to the fatty-components. The cellular matter usually comprises 20 to 40 weight percent of the excretion of the sebaceous glands. The broad variation results from age and health differentials. The amount of water in sebum is also subject to variation due to metabolism, thermal controls and the sterol content of the fatty components.

In addition, small amounts of complex sugars from the decomposition of glycoprotein are present. These are oligomers of glycogen. Cerumen contains much of such sugars.

The composition of human sebum is subject to much variation between individuals and between areas of the body as well as a result of dietary variations. Vitamin A and Vitamin E have been reported to change the proportions within the composition of the fatty components of sebum. A representative analysis of the fatty components of sebum is represented in Table I below:

TABLE I

| Composition of Human Sebum | |
| --- | --- |
| Free fatty acids (saturated) | 14.3% |
| Free fatty acids (unsaturated) | 14.0 |
| Triglycerides | 32.5 |
| Waxes (excluding cholesterol esters) | 14.0 |
| Free cholesterol | 2.0 |
| Cholesterol esters | 2.1 |
| Other sterols | 0.4 |
| Squalene ($C_{30}H_{50}$) | 5.5 |
| Paraffins (branched chains) | 8.1 |
| $C_{14}$ to $C_{24}$ alkane-diols | 2.0 |
| Not specified | 5.1 |

Generally it is desired to remove accumulated total sebum from the skin and hair. The use of soaps and other detergents as surfactant materials generally emulsifies the fatty materials in a more or less satisfactory manner. During this emulsification the cellular debris is also loosened and upon rinsing the skin and hair is cleansed. However the use of soaps or detergents has a drying effect upon the skin surface. The emollience of the skin is removed together with the normal moisture. The skin and hair are thus excessively dried leading to separate complicating cosmetic problems.

OBJECTS OF THE INVENTION

It is an object of this invention to break down the fatty components of sebum at the skin surface and cosmetically improve the appearance thereof. It is another object of this invention to promote debridment of the cellular remnants in the sebum by decomposing them from proteinaceous cellular remnants to smaller molecular fractions of a more liquid nature with lesser tendency to clog the glandular portals or exfoliate on dark clothes. It is also an object to promote the breakdown of complex sugar oligomers at the skin surface to facilitate cleansing of surfaces and to improve the appearance thereof.

These and other cosmetically desireable objects are achieved by my invention.

THE INVENTION

The present invention is based upon cosmetically effective compositions which comprise enzymes, useful for the degradation of sebum and sweat residue on the skin, in immobilized form, in cosmetically acceptable vehicles. The enzymes are immobilized in known manners, depending on the enzyme and the vehicle, and the composition is applied to the skin in problem areas. As a result of contact with the substrate of skin coated with excreted sweat and sebum residues, the enzymes are remobilized. The released enzymes specifically catalyze the breakdown to lower molecular weight molecules of the fats, proteins and sugar oligomers. Generally the compositions should contain lipase in immobilized form as the fatty components of sebum are most undesireable from a cosmetic point of view.

The fats from sebum tend to adsorb and absorb solids which then form crusts and flakes. They also form shiny residual layers on the skin. On the hair, these fats attract and hold dirt, cause matting and emit a characteristic odor. Despite the fact that such odor is postulated to possess characteristic pheromones, it is upon air-oxidation considered to be esthetically undesirable.

The lipase, when activated from its immobilized form, breaks down the lipid components of sebum, either linear fatty acid esters, fatty acids or polycylic cholesterols, to lower molecular weight compounds. Some of these products are also partially oxidized by the action of the lipase to form simple alcohols, aldehydes as well as hydrocarbons.

The cellular remnant portion of sebum is primarily proteinaceous. When these dead cells are exposed to proteases released fom immobilizing carriers, the proteins are broken down. The products of the action of proteases on protein substrates are well known, ranging from polypeptides to the ultimate amino-acid building blocks.

In addition, glycoproteins excreted either with the sebum or sweat, are readily broken down by glycases alone or in combination with proteases to protein decomposition products and simple sugars.

All the above decomposition products, from the action of immobilized enzymes in the composites of this invention are liquids and water soluble thus providing for ease of removal by washing and rinsing.

From a cosmetic point of view the biggest problem is the fatty component of sebum. Immobilized lipases thus are an important component of cosmetics to be applied to skin areas where sebum is the major exudate. However, as cellular exfoliation is an overall phenomenon of skin catabolism, it is useful to also include immobilized proteases and glycases to take care of these conditions. Thus the invention also includes the concept of including several immobilized enzymes in the cosmetic compositions of this invention.

In the broadest aspects, this invention contemplates the application of immobilized enzyme compositions via cosmetically acceptable vehicles to the skin surface where the enzymes are mobilized or re-activated to react with the skin secretions on or at the surfaces exposed to the application of the composition. The vehicle can contain the immobilized enzyme in particulate form either as a solid or liquid. The vehicle should preferably be either inactive with respect to the immobilized enzyme or should be part of the immobilizing actives of the immobilizing enzyme. The composition should activate to release the enzyme on contact with the residue substrates upon which the enzymes should act. Thus the enzymes are mobilized upon contact with either the lipids, exfoliated cells or sugar oligomers (glycoproteins).

DETAILED DESCRIPTION AND DEFINITIONS OF THIS INVENTION

The term immobilized enzymes as herein used refers to complexes of enzymes with physical or chemical phases and agents which hold or confine the enzyme in inactive or slightly active form until mobilized to utilize the specific activity of the enzyme. Various specific mechanisms for physical and/or chemical immobilization of immobilized enzymes are set forth by ZABORSKY, O. R. "Immobilized Enzymes" (CRC Press, Cleveland, Ohio, 1973) and subsequent articles dealing with this subject.

The types of chemical enzyme immobilization generally consist of (a) attachment and conjugation of the enzyme to a functional polymer; (b) incorporation of the enzyme into the growing polymer chain; (c) cross-linking of the enzyme into the polymer matrix.

The most commonly employed method for preparing enzyme polymer conjugates consists of contacting a solubilized enzyme with a functionalized reactive polymer. The conjugation may be either by (a) grafting (b) copolymerization and (c) a combination of (a) and (b) which is covalent bonding with entrapment of the enzyme.

During this conjugation the choise of polymer and enzyme is predicated upon functional groups of the enzyme that are not essential for catalysis and those, if reacted, would not detrimentally effect any desireable catalytic properties of the enzyme. The polymeric supports may be either synthetic or natural. Among the synthetic materials for conjugation are acrylamide-based polymers, maleic anhydride-based polymers, polyvinyl pyrrolidone, built polypeptides and styrene based polymers. Among natural supports for immobilization are celluloses, agaroses, dextrans, carragheenans, starches, and polypeptides from protein degradation, and others.

The cross-linking immobilization of enzymes is accomplished by the use of multifunctional reagents for the polymerization. By proper choice of reagent, and enzyme concentration, pH, and ionic strength of the solution, the molecular weight and solubility (degree of immobilization) can range from soluble dimers and trimers thru slightly soluble oligomer complexes to three-dimensional crosslinked species that are insoluble. This method can be utilized to prepare various types of immobilized enzymes such as gels, membranes, adsorbed monolayers; and polymer-bound conjugates. The gels can be dispersed easily. The membranes and monolayers provide the characteristic advantages of such physical forms. The polymer-bound conjugates can easily be shaped or comminuted for special purposes.

The enzyme for immobilization may be physically immobilized by (a) adsorption of the enzyme unto an adsorbant matrix or substrate; (b) absorbtion of the enzyme into an absorbant matrix; (c) enclosure of the enzyme within the lattice of a gel or a high viscosity multiphase liquid; (d) confinement of the enzyme within a semipermeable micro-capsule; (e) confinement of the enzyme within a semi-permeable membrane; (f) positioning the enzyme within a liposome.

The enzyme element of the immobilized enzyme component in the composition of this invention can be any broad spectrum lipase, protease or glycase or specific enzymes from each class recognized and selected for its specific demonstrated activity against sebum components. These enzymes are commercially available in various grades. The food and medicinal grades are preferred for immobilization for the purposes of this invention.

The enzymes as they are immobilized do not penetrate the skin but are released or mobilized on the surface of the skin by contact with sebum.

Upon activation and mobilization, the enzymes act by splitting the large molecules of the sebum components secreted by the sebaceous glands into smaller non-fatty constituents. As this reaction takes place primarily at the surface of the skin, the composition of this invention are true cosmetics. If some penetration of the sebaceous ducts takes place with splitting of the various sebum molecules due to the inherent excretory flow of the sebum to the skin surface, no systemic effects result and the product remains within the ambit of "cosmetic preparation". As a result of the breakdown of the oily sebum and thus its conversion to non-oily components, the oily skin is modified to a normal skin.

The cosmetic and cleansing formulations from this invention include creams, lotions, make-ups (solid, liquid and semi-solid), toners, moisturizers, astringents, shampoos, hair lotions, hair stylers and conditioners. By their use, sebum exudate on the skin or hair is split to smaller non-fatty molecules which are cosmetically acceptable.

Generally, while most cosmetic vehicles are based on oleaginous bases or on emulsified oily materials; since lipases are included in the immobilized enzymes, it is preferred to formulate the vehicles with hydrocarbon oils of the mineral oil or petrolatum type. Certain saturated animal and vegetable oils and waxes and synthetic cholesterol-type complexes which are lipase-resistant may also be included in the formulations. Also satisfactory as cosmetic vehicles are gel-formulations with water or alcoholic solutions as diluents. The immobilized enzymes which are generally solid may be suspended with other solids or mixed into semi-solids in the form of make-up sticks, mud packs or poultice fillers. These are then applied to areas where the amount of sebum exudate requires removal.

The immobilized enzymes components of this invention are utilized in the vehicle at concentrations varying from 0.1 to 25 wt. percent of the final composition. The concentration used depends on the duration of intended contact of the composition upon the skin. Liquid or lotion preparations will have higher concentrations as their residual films may not endure on the surface and are readily followed by rinsing. Creams, ointments and gels which leave more durable films, preferably have lower concentrations of the immobilized enzymes. Thick clays or night creams designed for contact with the skin surfaces for longer times can have the lower concentration but mud pack vehicles designed for temporary application can have higher concentrations. The broadest concentration of the immobilized enzymes range from 0.1 to 25% with 0.5 to 15% being preferred. Concentration of from 1% to 15% are preferred for short-term topical applications but longer term application should have concentrates of from 0.5 to 5%.

Concentrations can also vary depending upon the degree of immobilization of the enzyme and the ease with which it is released upon contact with the skin. As activity varies between enzymes of each class, this too requires adjustment in vehicles, immobilization form and concentration.

A convenient release mechanism for mobilizing the enzyme from its immobilized form is variation in pH upon contact with the skin. As the skin surface is buffered to pH in the range 4.5 to about 6, it is useful to have the enzymes activated by contact within this range. Generally many immobilized enzyme moieties are pH labile and can be adjusted to release the enzymes upon contact with the skin.

The invention will be further examplified by the appended examples detailing formulae of compositions embodying this invention. These formulae represent presently preferred compositions. The invention is, of course, not limited to the specific embodiments shown and described. Some of the described ingredients may be substituted by art-recognized equivalents or their concentrations changed or otherwise modified without departing from the spirit and scope of the appended claims.

EXAMPLES

EXAMPLE 1

|  | Wt. % |
| --- | --- |
| Oil Phase |  |
| Immobilized Lipase | 2.5 |
| Arlacel 83 | 3.0 |
| Paraffin | 10.0 |
| Light Mineral Oil | 15.0 |
| Petrolatum | 32.5 |
| Atlas G 1425 | 4.0 |
| Propyl Paraben | 0.15 |
| Aqueous Phase |  |
| Methyl Paraben | 0.15 |
| Sorbitol | 2.5 |
| Water | 29.+ |
| Perfume q.s. |  |

The water and oil phases are heated to about 65° C. and the water is slowly added to the stirred oil. The resultant w/o emulsion provides a smooth thick cream which leaves an adherent film on the skin providing intimate contact of the enzyme on the skin surface.

EXAMPLE 2

| Immobilized lipase protease mixture (from pancreatic liquid) | 3% |
| --- | --- |
| K Y Jelly (Johnson & Johnson) | 97 |

The immobilized enzyme mixture is ground into the jelly until uniformly distributed. The final gel provides an adherent lubricating gel that spreads easily on the skin and relases enzyme on contact with the slightly acidic skin.

EXAMPLE 3

| Oil Phase |  |
| --- | --- |
| Immobilized lipase | 1.5% |
| Atlas G 1726 | 1.5 |
| Atlas G 1702 | 3.5 |
| Paraffin | 10.5 |
| Light Mineral oil | 30.0 |
| Velvasil silicone fluid 1000 | 10.0 |
| Propyl Paraben | 0.15 |
| Water Phase | 0.15 |
| Methyl Paraben |  |
| Borax | 0.18 |
| Glycerol | 5.0 |
| Water | 37.0 |
| Perfume q.s. |  |

This formula provides an o/w creme that spreads easily and leaves a satisfactory oil-based film containing the enzyme for slow release at the skin surface.

EXAMPLE 4

| Immobilized Lipase and Protease Powder (from B. Subtilis cultures) | 2.0 |
| --- | --- |
| Glycerol | 18.0 |
| Alcohol (SD 25) | 80.0 |
| Perfume q.s. |  |

The powdered enzyme is ground into the glycerol and then the alcohol is added. The astringent liquid, when applied, leaves a hygroscopic layer containing the enzymes which are released on the skin or hair.

EXAMPLE 5

| Immobilized Lipase | 10% |
| --- | --- |
| Petrolatum (Vaseline) | 20% |
| Paraffin | 3% |
| Liquid Petroleum | 67% |

The immobilized lipase is milled with the petrolatum until uniformly comminuted and dispersed. The mineral oil and paraffin are heated until the paraffin dissolves. This solution is then milled with enzyme dispersion. As the semi-solid is cooled, the perfume and colorants are added. The resultant unguent is useful for application to the skin and hair where it leaves a thin film of the enzyme which is mobilized on contact with the skin.

EXAMPLE 6

| | |
|---|---|
| Immobilized Lipase | 20% |
| Mud pack clay solids | 80% |

The powdered immobilized enzyme is well-mixed with mud pack solids. The mixed powders are wetted with mud pack liquids to form a paste for application to the face. The paste is dried in situ and is washed off after 15 to 60 minutes.

EXAMPLE 7

| | |
|---|---|
| Immobilized Lipase/protease powder | 0.5% |
| Ethanolic solution of hair conditioner based on polyelectrolyte | 99.5% |

The immobilized enzyme powder is suspended in the viscous conditioner solution which is then further diluted before bottling in spray bottles. The conditioner is applied to the hair and scalp. It controls the hair setting, movement and texture as well as breaking down the oil and dandruff on the hair and scalp.

EXAMPLE 8

| | |
|---|---|
| Immobilized Lipase-protease powder | 0.7% |
| Mineral Oil, light | 23.5 |
| Ozokerite mp 75–80 | 5.0 |
| Petrolatum | 46.8 |
| Ethoxylated lanolin | 4.0 |
| Paraffin mp 56–58° C. | 5.0 |
| Colorants (TiO$_2$, pigments, Talc) | 15.0 |
| Perfume qs | |

Heat the ointment until melted and mill in the dry ingredients until a uniform mixture is obtained. The resultant foundation cream is applied over the face and neck providing cosmetic coloration and sebum breakdown.

I claim:

1. A cosmetic composition for cosmetically removing sebum containing an effective amount of an immobilized lipase enzyme, in a cosmetically-acceptable vehicle for topical application to the skin and/or hair, to enzymatically split fatty components and cellmolecular remnants in sebum to smaller molecular fragments.

2. The composition according to claim 1 and further including immobilized glycases, proteases and mixtures thereof, with the immobilized lipase.

3. The composition according to claim 1 wherein said enzyme is chemically immobilized by at least one of (a) attachment of the enzyme to a functionalized polymer or (b) incorporation of the enzyme into a polymer-chain or (c) the enzyme is cross-linked into the polymer matrix.

4. The composition according to claim 1 wherein said enzyme is physically immobilized by at least one of (a) adsorption of the enzyme into an adsorbent matrix or (b) absorbtion into an absorbent matrix or (c) enclosure of the enzyme within the lattice of a gel or high-viscosity multiphase liquid or (d) confinement of the enzyme within semipermeable microcapsules or (e) confinement of the enzyme within a semipermeable membrane or (f) positioning of the enzyme within a liposome.

5. The composition according to claim 1 wherein said immobilized enzyme is suspended and dispersed in a lipid-free cosmetically acceptable vehicle.

6. The composition according to claim 1 wherein said cosmetically acceptable vehicle is a diluted gel lattice substantive to the skin and capable of positioning of the immobilized enzyme suspended therein at the desired topical location to maintain said enzyme at the surface of the skin during the functioning of said immobilized enzyme on the skin secretions.

7. The composition according to claim 5 wherein said lipid-free vehicle is a petroleum hydrocarbon of cosmetic grade.

8. The composition according to claim 7 wherein said petroleum is a liquid mineral oil.

9. The composition according to claim 7 wherein said petrolatum is a semi-solid petrolatum.

10. The composition according to claim 1 wherein said vehicle is a lipid-free hair-dressing for maintaining contact of said enzyme at the hair surface during its local mobilization and performance of splitting function on the sebaceous secretions thereof.

* * * * *